United States Patent
Tjärnehov et al.

(10) Patent No.: US 12,415,724 B2
(45) Date of Patent: Sep. 16, 2025

(54) METHOD FOR THE PREPARATION OF SYNTHESIS GAS

(71) Applicant: Topsoe A/S, Kgs. Lyngby (DK)

(72) Inventors: Emil Andreas Tjärnehov, Limhamn (SE); Pat A. Han, Smørum (DK)

(73) Assignee: Topsoe A/S, Kgs. Lyngby (DK)

( * ) Notice: Subject to any disclaimer, the term of this patent is extended or adjusted under 35 U.S.C. 154(b) by 584 days.

(21) Appl. No.: 17/800,165

(22) PCT Filed: Feb. 24, 2021

(86) PCT No.: PCT/EP2021/054520
§ 371 (c)(1),
(2) Date: Aug. 16, 2022

(87) PCT Pub. No.: WO2021/170628
PCT Pub. Date: Sep. 2, 2021

(65) Prior Publication Data
US 2023/0109188 A1  Apr. 6, 2023

(30) Foreign Application Priority Data

Feb. 28, 2020 (DK) .............. PA 2020 00259

(51) Int. Cl.
*C01B 3/38* (2006.01)
*C07C 29/151* (2006.01)
*C25B 1/04* (2021.01)

(52) U.S. Cl.
CPC .......... *C01B 3/382* (2013.01); *C07C 29/1518* (2013.01); *C01B 2203/0233* (2013.01); *C01B 2203/0244* (2013.01); *C01B 2203/061* (2013.01); *C01B 2203/0833* (2013.01); *C01B 2203/1241* (2013.01); *C25B 1/04* (2013.01)

(58) Field of Classification Search
CPC .......... C25B 1/04; C25B 1/042; C01B 3/382; C01B 29/1518; C01B 2203/0233; C01B 2203/0244; C01B 2203/061; C01B 2203/0833; C01B 2203/1241; C01B 2203/1276

See application file for complete search history.

(56) References Cited

U.S. PATENT DOCUMENTS

| | | | |
|---|---|---|---|
| 2015/0184082 A1* | 7/2015 | Iijima | C10L 1/06 585/324 |
| 2017/0002281 A1 | 1/2017 | Aasberg-Petersen et al. | |

FOREIGN PATENT DOCUMENTS

| | | |
|---|---|---|
| EP | 1 698 590 A1 | 9/2006 |
| WO | WO 2013/013895 A1 | 1/2013 |
| WO | WO 2014/209605 A1 | 12/2014 |
| WO | WO 2015/086752 A1 | 6/2015 |
| WO | WO 2019/011659 A1 | 1/2019 |
| WO | WO 2019/020376 A1 | 1/2019 |
| WO | WO 2019/020377 A1 | 1/2019 |
| WO | WO 2019/020378 A1 | 1/2019 |
| WO | WO 2019/020513 A1 | 1/2019 |
| WO | WO 2019/020515 A1 | 1/2019 |
| WO | WO 2019/020519 A1 | 1/2019 |

* cited by examiner

*Primary Examiner* — Jafar F Parsa
(74) *Attorney, Agent, or Firm* — Blank Rome LLP

(57) ABSTRACT

Method for the preparation of synthesis gas combining electrolysis of water, tubular steam reforming and autothermal reforming of a hydrocarbon feed stock in parallel.

7 Claims, No Drawings

METHOD FOR THE PREPARATION OF SYNTHESIS GAS

The present application is directed to the preparation of synthesis gas. More particular, the invention combines electrolysis of water, tubular steam reforming and autothermal reforming in parallel and optionally additionally heat exchange reforming of a hydrocarbon feed stock in the preparation of a hydrogen and carbon oxides containing synthesis gas.

Preparation of synthesis gas e.g. for the methanol synthesis is typically carried out by steam reforming of hydrocarbons.

The principal reaction of steam reforming is (given for methane):

$$CH_4 + H_2O \leftrightarrows 3H_2 + CO$$

Similar reactions occur for other hydrocarbons. Steam reforming is normally accompanied by the water gas shift reaction:

$$CO + H_2O \leftrightarrows CO_2 + H_2$$

Steam reforming is typically carried out by a combination of a tubular reformer (also called steam methane reformer, SMR) and autothermal reforming (ATR), also known as primary and secondary reforming or 2-step reforming. Alternatively, stand-alone SMR or stand-alone ATR can be used to prepare synthesis gas.

The main elements of an ATR reactor are a burner, a combustion chamber, and a catalyst bed contained within a refractory lined pressure shell. In an ATR reactor, partial oxidation or combustion of a hydrocarbon feed by substoichiometric amounts of oxygen is followed by steam reforming of the partially combusted hydrocarbon feed stream in a fixed bed of steam reforming catalyst. Steam reforming also takes place to some extent in the combustion chamber due to the high temperature.

In 2-step reforming the steam methane reformer (SMR) must be large and a significant amount of heat is required to drive the endothermic steam reforming reaction. Hence, it is desirable if the size and duty of the steam reformer can be reduced. Furthermore, the ATR in the 2-step reforming concept requires oxygen. Today this is typically produced in a cryogenic air separation unit (ASU). The size and cost of this ASU is large. If the oxygen could be produced by other means, this would be desirable.

SMR produces hydrogen in excess to what is required for a suitable methanol synthesis gas composition, while ATR produces hydrogen in less amounts.

We have found that when combining tubular steam reforming and autothermal reforming in parallel together with electrolysis of water and/or steam, oxygen from the electrolysis can be used in the ATR and the expensive ASU becomes superfluous in the preparation of synthesis gas.

At the same time, hydrogen from electrolysis contributes to the hydrogen required for methanol production, which will allow for addition of additional carbon dioxide to the process still resulting in a module required for methanol synthesis.

Thus, this invention provides a method for the preparation of synthesis gas comprising the steps of
(a) providing a hydrocarbon feed stock;
(b) preparing a separate hydrogen containing stream and a separate oxygen containing stream by electrolysis of water and/or steam;
(c) steam reforming a first part of the hydrocarbon feed stock from step (a) in a tubular steam reformer to a tubular steam reformed gas comprising hydrogen, carbon monoxide and carbon dioxide;
(d) autothermal reforming a second part of the hydrocarbon feed stock in an autothermal reformer with at least part of the oxygen containing stream obtained in step (b) to an autothermal reformed gas stream comprising hydrogen, carbon monoxide and carbon dioxide;
(e) combining the steam reformed gas from step (c) with the autothermal reformed gas from step (d);
(f) adding at least part of the separate hydrogen containing stream from step (b) into the hydrocarbon feed stock from step (a) and/or into the steam reformed gas stream from step (c) and/or into the autothermal reformed gas stream from step (d) and/or into the combined steam reformed gas and autothermal reformed gas stream from step (e); and
(g) withdrawing the synthesis gas.

Tubular steam reforming creates $CO_2$ in the flue gas from the burners in the tubular steam reforming. The $Co_2$ in the flue gas is in an embodiment of the invention recovered and added to the tubular steam reforming process.

Thereby, the $CO_2$ footprint of the method according to the invention is advantageously lowered when the added $CO_2$ is utilized in the production methanol.

To minimize $CO_2$ emissions further, a part of the feedstock can be heat exchange reformed in a heat exchange reformer downstream the tubular steam reformer and/or the tubular steam reformed gas can be additionally heat exchange reformed to reduce fuel consumption.

The electrolysis can be performed by various means known in the art such as by solid oxide based electrolysis or electrolysis by alkaline cells or polymer cells (PEM).

When the power for the electrolysis is produced (at least in part) by sustainable sources, the $CO_2$-emissions is per unit of product produced by the method reduced.

Preferably, the electrolysis of water and/or steam is powered solely by renewable energy.

As already mentioned above, all the oxygen from the electrolysis unit is added to the autothermal reformer in step (d) and an ASU for the preparation of oxygen by separation of air is avoided.

The method according to the invention is preferably employed for the production of methanol synthesis gas.

Methanol synthesis gas has preferably a composition corresponding to a so-called module (M=(H2−CO2)/(CO+CO2)) of 1.90-2.20 or more preferably slightly above 2 (eg. 2.00-2.10).

Thus when the method according to the invention is used in the preparation of methanol synthesis gas, the amount of hydrogen added to the feed stock upstream to the SMR or the ATR or to the reformed gas downstream step (e) can be tailored such that when the hydrogen is mixed with the synthesis gas generated by the reforming steps and the optionally $CO_2$ addition recovered from the tubular steam reformer a desired value of M of between 1.90 and 2.20 or preferably between 2.00 and 2.10 is achieved.

In general, suitable hydrocarbon feedstocks for use in the various embodiments of the invention comprise natural gas, methane, LNG, naphtha or mixtures thereof either as such or pre-reformed and/or desulfurized.

The method according to the invention can also be employed for producing synthesis gas for other applications where it is desirable to increase the hydrogen concentration in the feed gas and where the hydrogen and oxygen is favorably produced by electrolysis.

The invention claimed is:

1. Method for the preparation of synthesis gas comprising the steps of:
   (a) providing a hydrocarbon feed stock;
   (b) preparing a separate hydrogen containing stream and a separate oxygen containing stream by electrolysis of water and/or steam;
   (c) steam reforming a first part of the hydrocarbon feed stock from step (a) in a tubular steam reformer to a tubular steam reformed gas comprising hydrogen, carbon monoxide and carbon dioxide, including recovering carbon dioxide in flue gas from burners in the tubular steam reformer and adding the recovered carbon dioxide to the steam reforming process;
   (d) autothermal reforming a second part of the hydrocarbon feed stock in an autothermal reformer with at least part of the oxygen containing stream obtained in step (b) to an autothermal reformed gas stream comprising hydrogen, carbon monoxide and carbon dioxide;
   (e) combining the steam reformed gas from step (c) with the autothermal reformed gas from step (d);
   (f) adding at least part of the separate hydrogen containing stream from step (b) into the hydrocarbon feed stock from step (a) and/or into the steam reformed gas stream from step (c) and/or into the autothermal reformed gas stream from step (d) and/or into the combined steam reformed gas and autothermal reformed gas stream from step (e); and
   (g) withdrawing the synthesis gas.

2. The method of claim 1, wherein the electrolysis of water and/or steam in step (b) is powered by renewable energy.

3. The method of claim 1, wherein the hydrogen stream is added to the combined tubular steam reformed gas and autothermal reformed gas stream in an amount to provide a module $M=(H_2-CO_2)/(CO+CO_2)$ in the synthesis gas withdrawn in step (g) of between 1.9 and 2.2.

4. The method of claim 1, wherein the module $M=(H_2-CO_2)/(CO+CO_2)$ in the synthesis gas withdrawn in step (g) is in the range from 2 to 2.1.

5. The method of claim 1, comprising the further step of heat exchange reforming a part of the hydrocarbon feedstock from step (a) and/or the tubular steam reformed gas from step (c).

6. The method of claim 1, wherein the hydrocarbon feed stock comprises natural gas, methane, LNG, naphtha or mixtures thereof either as such or pre-reformed and/or desulfurized.

7. The method of claim 1, wherein the synthesis gas withdrawn in step (g) is in a further step converted to a methanol product.

* * * * *